March 2, 1971 SEIZO SUZUKI Plant Pat. 3,033
ROSE PLANT
Filed Oct. 16, 1968
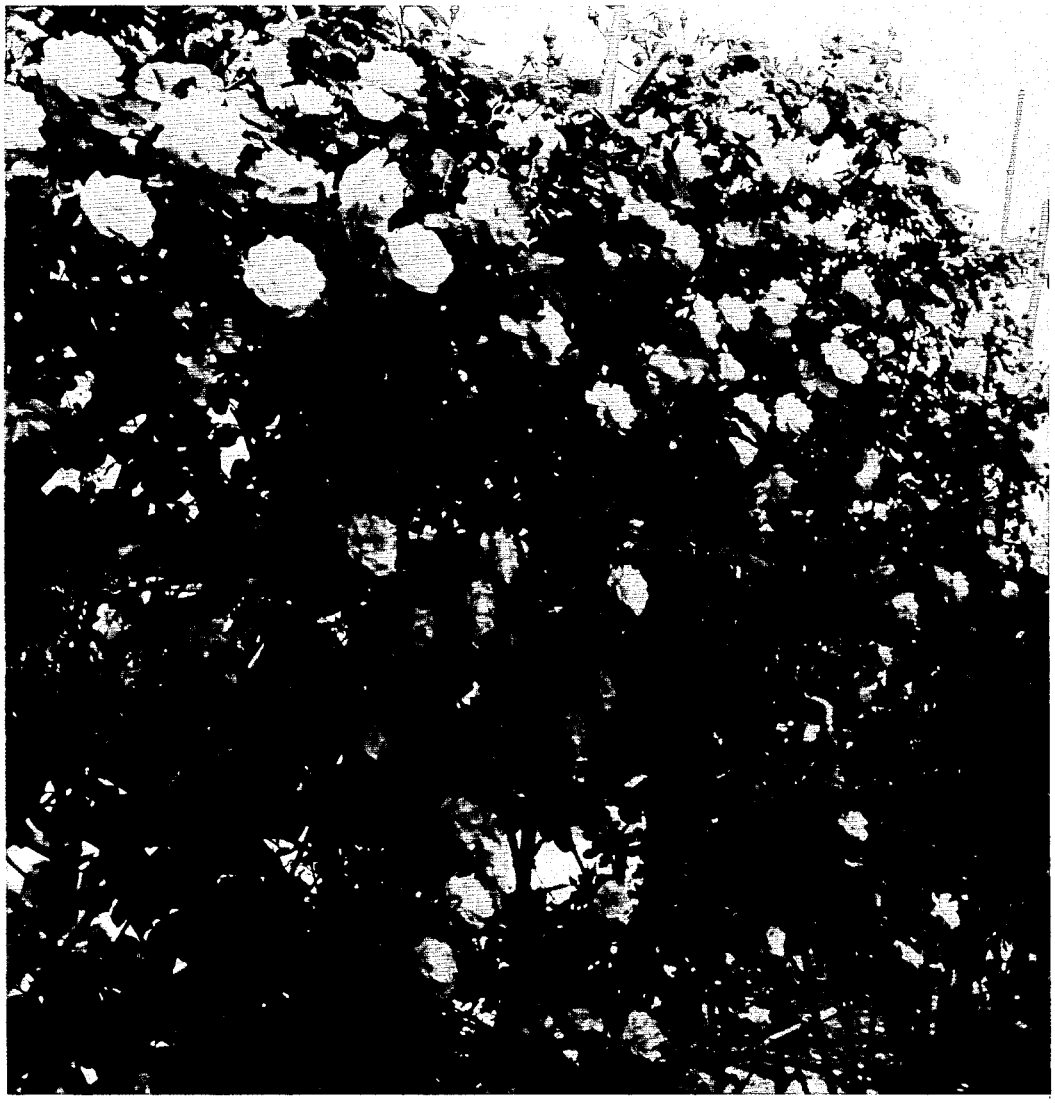

United States Patent Office

Plant Pat. 3,033
Patented Mar. 2, 1971

3,033
ROSE PLANT

Seizo Suzuki, 324, 3-chome, Tamayawa-Okusawa-cho, Setagaya-ku, Tokyo, Japan

Filed Oct. 16, 1968, Ser. No. 768,199
Int. Cl. A01h 5/00
U.S. Cl. Plt.—6 1 Claim The invention relates to a new and distinct variety of rose plant of the climber class originated by me in 1958 as a consequence of a breeding program begun in 1956. The parentage of my new rose plant is as follows:

Spectacular (P.P. 1416) × Aztec (P.P. 1648).

The object of the cross was to get a moderate-height, blooming climber which bears recurrent, large, bright, orange-vermilion flowers and also at getting a vigorous, disease-resistant plant with beautiful foliage.

These objectives were achieved along with other desirable improvements, as evidenced by the following unique combination of characteristics which are outstanding in the new variety and which distinguish it from its parents as well as from all other varieties of which I am aware. My new variety is primarily characterized by: large flowers in unique color which are produced recurrently and the petals of which fall clear after full blooming, without retaining dirty remnants.

Asexual reproduction of my new variety by budding and grafting through a series of annual propagations at Owaca, Yachiyo-shi, Chiba Prefecture, Japan shows that all characteristics of the variety come true to form through succeeding propagations. The accompanying photographs illustrate the primary characteristics of my new variety as nearly true as is reasonably possible to make them with presently available techniques. The color references cited are those of the Horticultural Colour Charts of the Royal Horticultural Society.

The following botanical description is based upon observation of field and container grown plants under greenhouse and field conditions at 555 Irwin Lane, Santa Rosa, Sonoma County, Calif. and Owada, Yachiyo, Chiba-Prefecture, Japan.

Vigorous, strong, arching plant to 7–10′ with slight to moderate branching. Abundant foliage, leaf odd pinnate. 3–7 leaflets, average 5, generally elliptic with pointed tip and serrated margins. Smooth, leathery, semi-glossy to glossy, ½–1½″ wide x ¾–1¾″ long. New leaflets are Fern Green (HCC 0862) on upper side, Willow Green (HCC 000862/1) on lower side. Old leaflets are Spinach Green (HCC 0960) on upper side, Willow Green (HCC 000862) on lower side. Petioles are ⅝–1″ in length. Rachis is 1⅛–2⅛″ in length, moderate amount of very small capitate prickles on upper surface, 4–5⅛″ hooked thorns on under surface; very few small capitate prickles. Ribs and veins conspicuous. Plant has thorns and prickles. Average of 4 per internode. Young thorns are Amber Yellow (HCC 505), old thorns are pinkish tan. Thorns are 3/32–⅛″ wide x ⅛–½″ tall x 3/16–⅜″ long, hooked, with point generally extending to almost the lower edge of the thorn. Canes are Fern Green (HCC 0862) when new and Fern Green (HCC 0862/1) when old.

The flower bud is long and pointed becoming urseolate. Of medium size, 1–1½″ in length, ½–⅝″ in diameter. Opens slowly. When sepals first divide the bud is Spinel Red (HCC 0023); when sepals begin to unfurl the bud is Spinel Red (HCC 0023). Sepals curl back as they unfurl, are not appendaged and have moderate to heavy branching. The inside is Fern Green (HCC 0862) and Lettuce Green (HCC 861) outside. Hypanthium is funnel-form of medium size, ⅜″ wide x ¼″ long. The outside is smooth, the inside hairy. Peduncle is 1⅛–1⅝″ in length, strong, erect and has some prickles (capitate). Lettuce Green (HCC 861).

The blooming habit of the flower is recurrent, intermittent. Plant blooms most profusely on 2 year-old wood, sparsely on new wood. Blooms of medium size, 4–4½″ in diameter x 1–1¼″ in depth, borne singly on short-medium shoots 3–10″ bearing 2–8 leaves, arising from almost every node along the main cane. Plant blooms from apical end of main cane first and progresses to the distal end. Blooms are moderately high centered when bloom first opens. Flattens somewhat as bloom matures. Petals are imbricated. 10–15 in number, obovate, almost leathery. Velvety to waxy in appearance, 1½–2″ wide x 1¾–2¼″ long. Outer petal is Blood Red (HCC 820/4), reverse Spinel Pink (HCC 0625); inner petal is Blood Red (HCC 820/2), reverse Spinel Red (HCC 0023). Slight fading after full bloom. Persists 5–10 days on stem. Petaloids (staminodia) are ¾–1½″ wide x 1½–1¾″ long. 5–7 in number with the same color as inner petals. Stamens (anthers) about 120 in number, about ½″ long with a whorled arrangement. Filaments about 7/16″ long, Spinel Red (HCC 0023/4). Pistils about 80 in number, about ¼″ long. Stigma is light pink like filaments. Styles are Cardinal Red (HCC 822/1). Disc very prominent. ⅜″ in diameter, ⅛″ high, 3/16″ thick, ivory white in color. Slight to moderate tea rose fragrance. Resistant to wet and hot weather. Resistant to mildew, above as observed at Santa Rosa, Calif. Pollen is orange. Very fertile. Fruit funnel-form, rounded, ¾–⅞″ in diameter with exserted red seeds.

Having thus disclosed my invention, I claim:

1. A new and distinct variety of rose plant of the climbing class substantially as herein shown and described primarily characterized by: the most early-blooming, large flowers in unique color which are produced recurrently and the petals of which fall clear after full blooming, without retaining dirty remnants.

No references cited.

ROBERT E. BAGWILL, Primary Examiner